United States Patent [19]

Collingwood

[11] 4,285,243
[45] Aug. 25, 1981

[54] ULTRASONIC PIPE INSPECTION APPARATUS

[75] Inventor: John C. Collingwood, Didcot, England

[73] Assignee: British Gas Corporation, London, England

[21] Appl. No.: 67,791

[22] Filed: Aug. 20, 1979

[30] Foreign Application Priority Data

Feb. 28, 1979 [GB] United Kingdom ............... 07148/79

[51] Int. Cl.³ ............................................. G01N 29/04
[52] U.S. Cl. ........................................ 73/623; 73/639
[58] Field of Search ................. 73/623, 638, 639, 633; 324/220; 250/358 P

[56] References Cited

U.S. PATENT DOCUMENTS

| | | | |
|---|---|---|---|
| 3,205,435 | 9/1965 | Nuttall | 324/220 |
| 3,413,653 | 11/1968 | Wood | 73/40.5 A |
| 3,478,576 | 11/1969 | Bogle | 73/40.5 A |
| 3,754,275 | 8/1973 | Carter et al. | 73/40.5 R X |
| 3,786,684 | 1/1974 | Wiers et al. | 73/432 R X |
| 4,055,990 | 11/1977 | Topping | 73/623 |
| 4,105,972 | 8/1978 | Smith | 73/638 X |
| 4,146,791 | 3/1979 | Dahl et al. | 250/358 P |
| 4,170,902 | 10/1979 | Pallan | 73/432 R |
| 4,217,782 | 8/1980 | Pont | 73/637 |

FOREIGN PATENT DOCUMENTS

| | | | |
|---|---|---|---|
| 369485 | 8/1973 | U.S.S.R. | 73/623 |
| 550573 | 8/1977 | U.S.S.R. | 73/623 |

Primary Examiner—Daniel M. Yasich
Attorney, Agent, or Firm—Watson, Cole, Grindle & Watson

[57] ABSTRACT

A pipe inspection device for ultrasonically inspecting the wall of a pipe includes a support arm which is pivotally attached at one end to an inspection vehicle and at its other end pivotally supports a spindle at the end of which two wheels are rotatably mounted. One or more ultrasonic transducers are disposed inside each wheel so that when the vehicle is moved along the pipe, the wheels come into contact with the pipe such that the transducers are aligned in predetermined positions relative to the pipe. The device may be arranged for insertion in the bore of the pipe, or for assembly around the outside of the pipe.

10 Claims, 5 Drawing Figures

ULTRASONIC PIPE INSPECTION APPARATUS

BACKGROUND OF THE INVENTION

1. Field of the Invention

This invention relates to an ultrasonic pipe inspection apparatus of the type which can be, for example, inserted into the bore of a pipe for the purpose of examining the wall of the pipes for defects, cracks or other discontinuities, and more particularly it relates to the wheel probes used in such apparatus for ultrasonically inspecting the pipe wall.

2. The Prior Art

The usual pipe inspection apparatus for examining, for example, gas pipelines, comprises a vehicle (or a train of vehicles) which is propelled along the pipeline by the gas flow in the pipeline. In one arrangement, the vehicle includes a number of wheels, in which are mounted ultrasonic transducers (usually referred to as "wheel probes") which are urged into contact with the wall of the pipe. In use, the ultrasound generated by the transducers is transmitted across the interface between the wheel probe and the wall of the pipe and into the pipe wall. The ultrasound reflected or refracted from within the pipe wall is in turn received by the transducers within the wheels and subsequently analyzed. This technique requires intimate contact at all times between the wheels and the pipe wall so as to reduce or eliminate losses of the ultrasound signal at the interface between the wheel and the pipe wall.

One form of known wheel probe comprises a hollow wheel assembly having an inflatable tire around its outer circumference, with the ultrasonic transducers being located within the wheel assembly, the sound being transmitted through the inflatable tire. In operation, the tire is urged into contact with the surface to be examined, and an acoustic coupling fluid is maintained between the inflatable tire and the surface to ensure that an adequate coupling is achieved.

In some applications it is impossible, or at least impractical, to use a coupling fluid between the inflatable tire and the surface to be examined. For example, when examining many miles of pipe lines conveying natural gas.

Realizing that there are instances when it is not possible to use a coupling fluid between the tire and the surface to be examined, the natural solution would be to force the inflated tire into dry contact with the surface. However, this requires the tire to be inflated to extremely high pressures to produce the forces required to ensure adequate contact between the tire and the surface.

In addition to the problem of inflating such tires to high pressures when examining many miles of gas pipe lines, other problems also result: the problem of wear of the tires, the problem of punctures caused by encountering sharp obstructions at some weldments, and the problem of tire construction (the material of the tire must be chosen so as not to be deleteriously affected by the gas flowing the pipeline).

An object of the present invention is to provide an improved wheel probe designed to remedy the aforesaid disadvantages and limitations of known wheel probes.

In U.S. patent application Ser. No. 933,031, filed Aug. 11, 1978, now abandoned, there is described a wheel probe for insertion into the bore of a pipe for the purpose of ultrasonically inspecting the wall of the pipe. The wheel probe comprises a solid annular rim made of a non-deformable material through which sound will pass, and side members which together with the rim define a hollow chamber. One or more ultrasonic transducers are located within the chamber and are positioned adjacent the inside surface of the rim for directing and receiving sound through the rim and a solid resilient tire member mounted on the outside surface of the rim.

In copending U.S. patent application Ser. No. 67,790, filed Aug. 20, 1979, an inspection apparatus is disclosed which includes a vehicle for movement along the bore of a pipe which will cater to bends in the pipe and, in some cases, will accommodate changes in the diameter of the pipe without upsetting, to an unacceptable degree, the alignment, positioning and degree of contact between wheel probes in the bore of the pipe.

It is essential to locate the wheel probes accurately in the bore of the pipe at all times, and in particular the wheel probes must be aligned so that the transducers are positioned at a predetermined angle to the tangent at the wall of the pipe so as to detect the echo or reflections or refractions of sound transmitted by that transducer or another transducer located in the same wheel probe or located in other wheel probes. Hence, it will be appreciated that it is usual to employ a plurality of wheel probes accurately positioned around the bore of the pipe which are arranged to roll along the length of the pipe. This accurate positioning may be achieved using guide wheels as described and claimed in U.S. Pat. No. 4,202,216.

The present invention dispenses with the need for guide wheels, and acknowledges that it is usual to position a plurality of wheel probes around the circumference of the pipe. The present invention also has as an object the provision of inspection devices which are self aligning relative to the pipe.

SUMMARY OF THE INVENTION

According to the present invention there is provided an inspection device for ultrasonically inspecting the wall of a pipe comprising a support means for attachment to a vehicle that in use is movable along the pipe, the support means carrying two spaced apart, hollow wheels, each wheel having one or more ultrasonic transducers located therein, the two wheels being mounted for rotation on a common spindle means which is itself pivotally mounted on the support means so that the spindle means pivots about an axis which extends in a direction normal to the axis of rotation of the wheels at a location intermediate the wheels, the ultrasonic transducers being positioned relative to the wheels so that in use they are aligned in predetermined positions relative to the geometry of the pipe.

The inspection device may be designed for insertion in the bore of the pipe in which case, in use, the wheels are urged into contact with the bore of the pipe. Alternatively, the inspection device may be designed for assembly around the outside of the pipe, in which case, in use, the wheels are urged into contact with the outside surface of the pipe wall.

The axes of rotation of the two wheels may lie on a common axis or on parallel axes. Alternatively, the axes of rotation of the two wheels may lie in angular relationship to each other. Preferably, each wheel rotates on an axis which extends parallel to the tangent line of the pipe wall at the point of contact between the wheel and the pipe. Also, each wheel will preferably be in a single plane which is normal to the longitudinal axis of the pipe. Two or more transducers may be arranged inside each wheel, with one transducer angled to direct, or receive, sound in one direction circumferentially through the wall of the pipe and another transducer angled to direct, or receive, sound in a second direction circumferentially through the pipe wall.

Preferably, the support means comprises an arm assembly which in use is pivotally mounted on the vehicle, the spindle means being mounted on the free end of the arm assembly in such a way that, in use, the wheels can be urged into contact with the pipe wall. Preferably a biasing means, such as a coil spring, is provided to operate on the arm assembly to urge the wheels into contact with the pipe wall.

The arm assembly may comprise two spaced apart arms and the common spindle means is pivotally mounted on the free ends of the two arms.

Preferably, guide means are provided for aligning the wheels in a preferred attitude relative to the pipe so that the wheels are aligned in the preferred attitude throughout the whole of the pivotal movement of the arm assembly.

When the axes of rotation of the wheels are on a common axis or on parallel axes, the array of transducers may be arranged asymmetrically inside each wheel. When each wheel rotates about an axis which lies in a single plane normal to the longitudinal axis of the vehicle, the array of transducers may be arranged symmetrically inside each wheel.

An embodiment of the present invention will now be described, by way of an example, with reference to the accompanying drawings;

DETAILED DESCRIPTION OF THE PREFERRED EMBODIMENT

Figure 1:
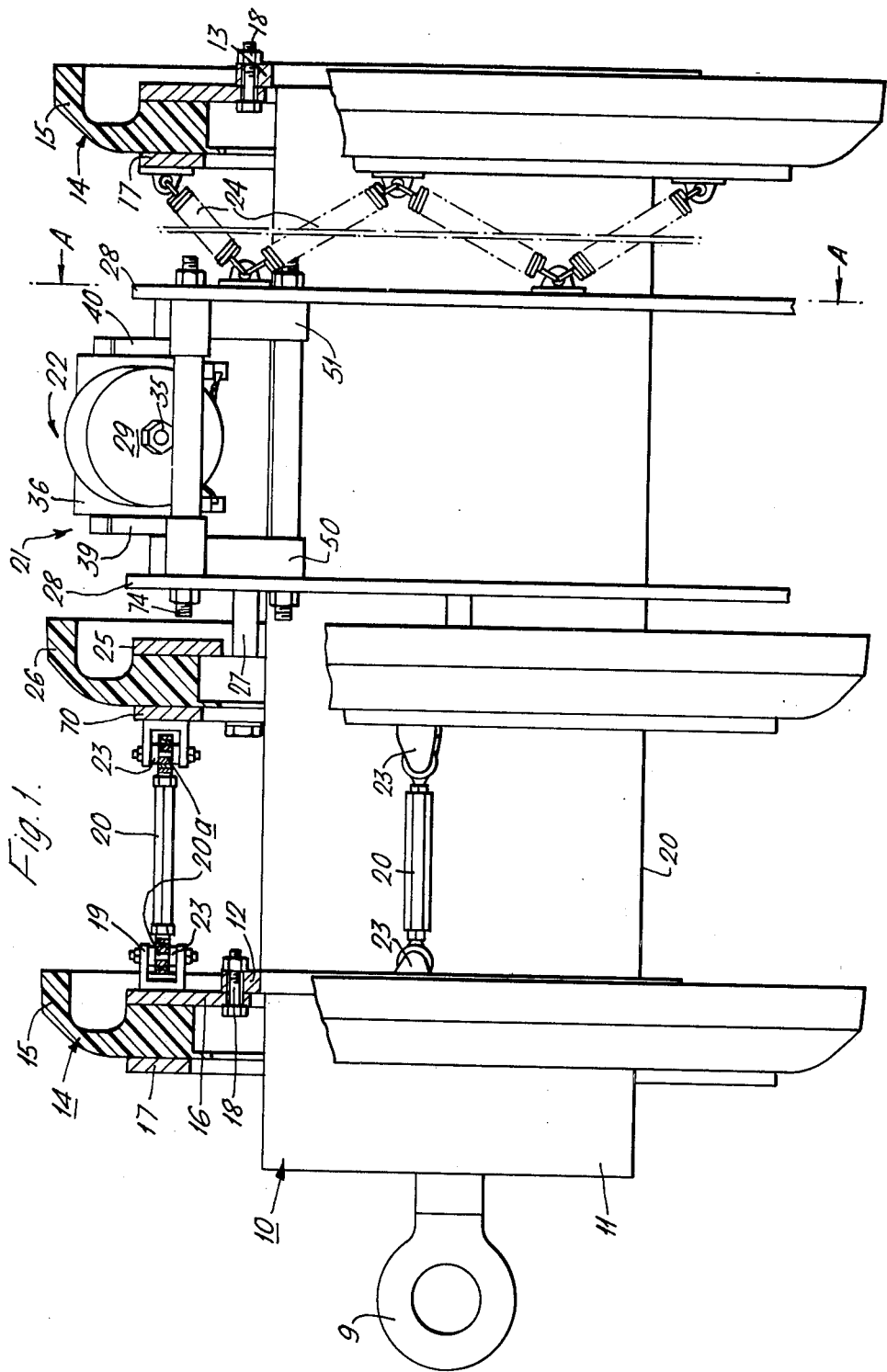
FIG. 1 shows a side elevational view, partly in section of an apparatus for ultrasonically inspecting the wall of a pipe incorporating a plurality of inspection devices constructed in accordance with the present invention.

Referring to FIG. 1, the apparatus, which is intended for insertion into a 24-inch diameter gas pipeline (not shown), comprises a vehicle 10 which is provided at one end with a towing eye 9 which enables the vehicle 10 to be towed by a second vehicle (not shown) which is propelled along the pipeline by the flow of pressurized gas in the pipe. The vehicle 10 is itself the subject of our co-pending U.S. patent application Ser. No. 67,790, filed on Aug. 20, 1979.

The vehicle 10 comprises a central hollow tubular member 11 having two flanges 12 and 13, each of which is located at or near respective ends of the vehicle. Alignment means 14 are mounted on each flange for the purpose of locating and aligning the vehicle 10 along the axis of the pipe. Each alignment means 14 comprises an annular sealing member 15 made of an elastomeric material such as polyurethane and has a concave recess facing towards the rear of the vehicle 10 so that pressurized gas in the pipe urges the sealing member 15 into engagement with the bore of the pipe. The annular sealing member 15 is clamped between an annular plate 16 and a clamping plate 17, and the annular plates 16 are secured by bolts 18 to the respective flanges 12, 13.

Four brackets 19 equispaced around a common pitch circle are secured to the front annular plate 16, and a link 20 is mounted by a spherical ball joint 20a at one end to a pivot 23 in each bracket 19 to provide the constraining means. A spherical ball joint 20a in the free end of each of the links 20 locates about a pivot 23 in a respective bracket 19 secured to an annular support plate 70, the brackets 19 being arranged so that the pivots 23 lie approximately radially relative to the front annular plate 16.

Figure 2:
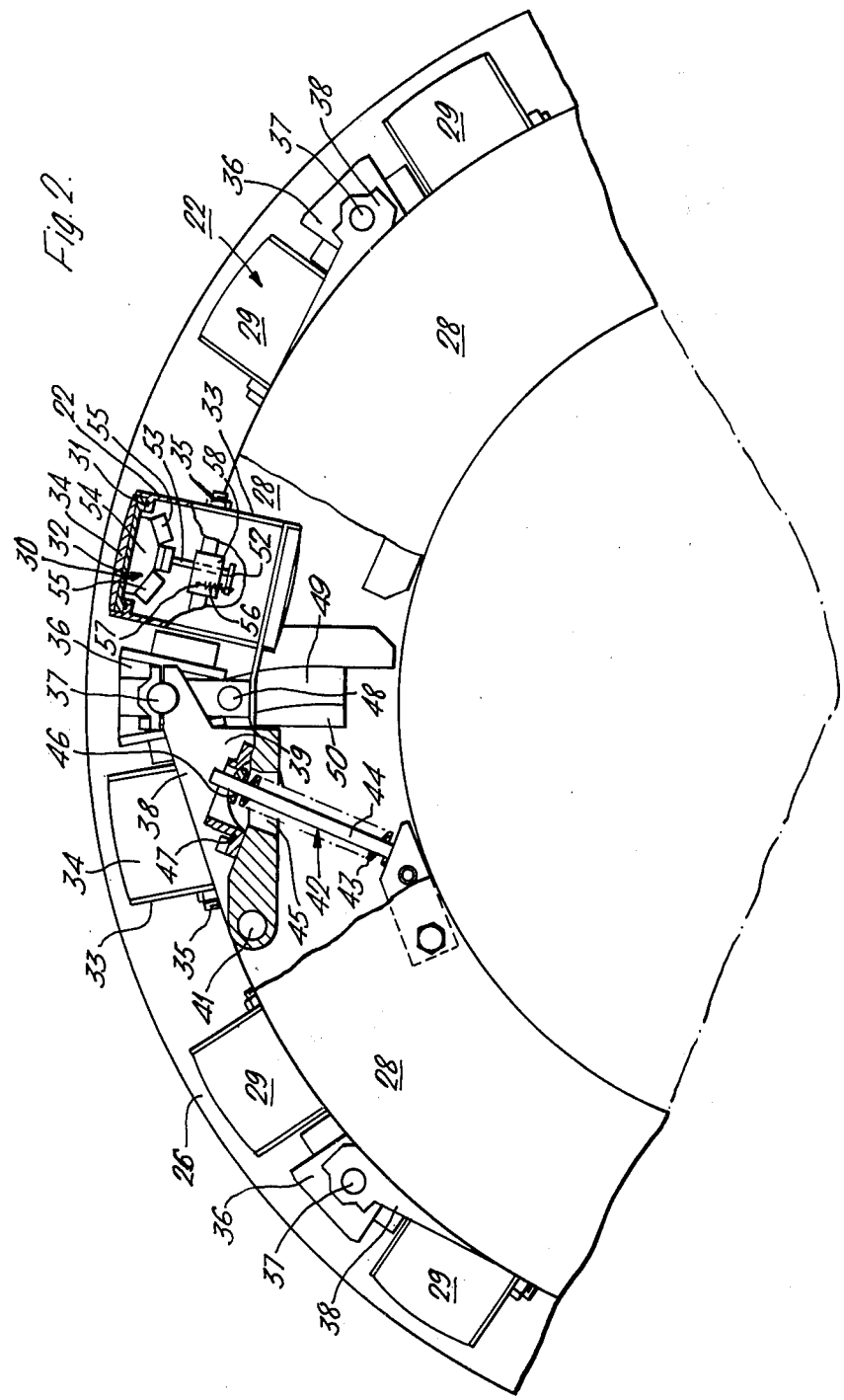
FIG. 2 shows a fragmentary, partly broken away end view of the apparatus of FIG. 1 looking along line A—A.

The support plate 70 forms part of a carrier 21 having two annular carrier plates 28 spaced apart in parallel relationship by hollow spacers 71 and secured together by bolts 74 extending through the spacers 71, the bolted-together carrier plates 28 being fixed to the support plate 70 by bolts 27. The carrier 21 is freely movable in a plane normal to the longitudinal axis of the vehicle 10, and is suspended on a spring 24 attached to the annular plate 17 of the rearmost alignment means 14 and the rearmost carrier plate 28. The carrier 21 has a rubber centralizing member 26 clamped between a clamping plate 25 and the support plate 70 to centralize the carrier 21 in the bore of the pipe. Eight inspection devices 22 are resiliently supported between the carrier plates 28, each being constructed as shown in greater detail in FIG. 2, to which reference is also made.

Figure 3:
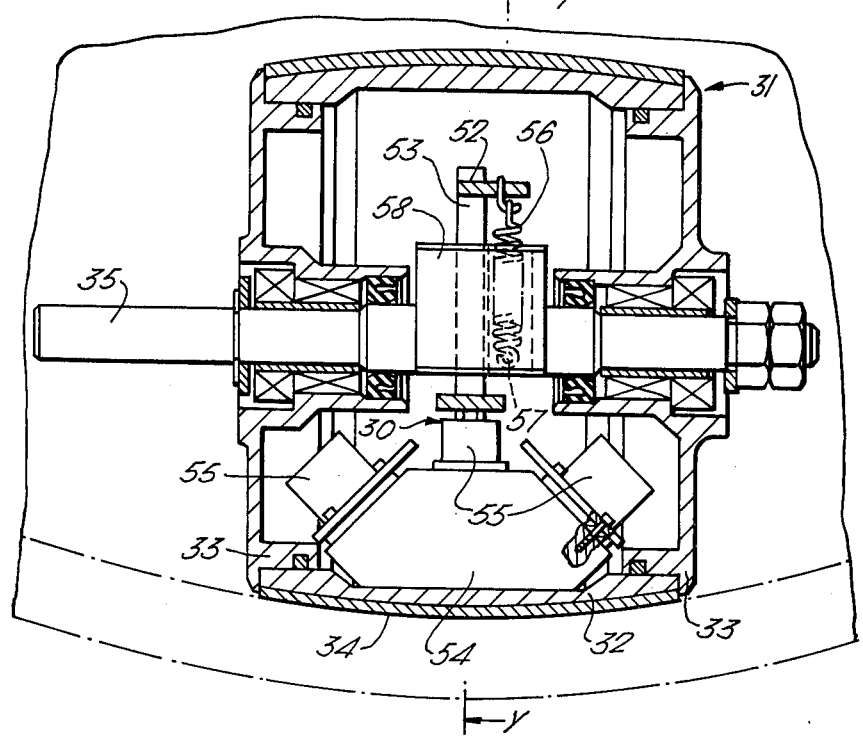
FIG. 3 shows a side elevational view, partly in section of one of the wheels of one of the inspection devices incorporated in the apparatus of FIG. 1.
Figure 4:
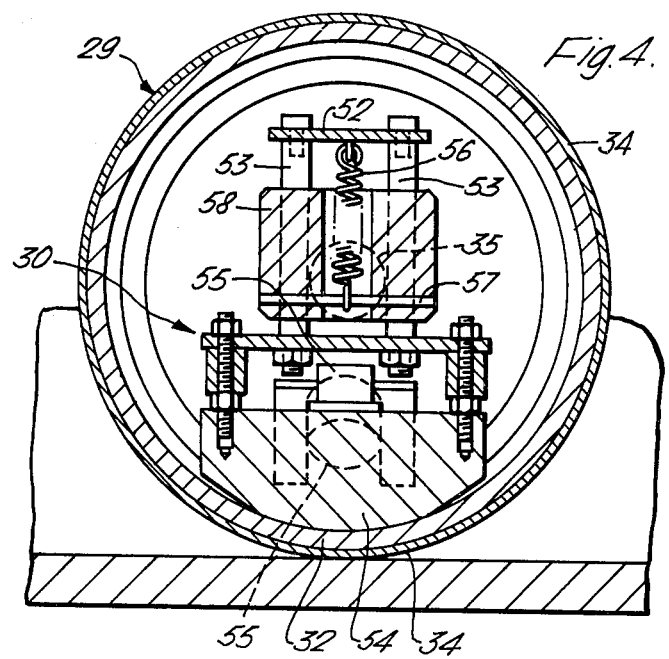
FIG. 4 shows a sectional end view of the wheel of FIG. 3 sectioned along line Y—Y of FIG. 3.

Each inspection device 22 comprises two hollow wheels 29, each wheel 29 having inside thereof an ultrasonic probe assembly 30 with transducers 55 arranged to transmit sound into the wall of the pipe so that the sound travels around a circumferential band of the pipe wall. Power for energizing the transducers 55, together with the signals representative of the sound received from within the pipe, are fed by way of leads (not shown) either to the towing vehicle or to a further vehicle (not shown) which is towed behind the vehicle 10. Each wheel 29 is shown in greater detail in FIGS. 3 and 4, and comprises an hermetically sealed hollow body 31 made of polymethylmethacrylate (Perspex—a Registered Trade Mark) rim 32 and brass side-plates 33 secured to the rim 32. The rim 32 is provided with a solid polyurethane tire 34 around its circumference. Each wheel 29 is mounted on bearings for rotation on a elongated mounting axle means 35 carried by a tapered block 36. "O" ring seals are provided between side-plates 33 and the rim 32 of each wheel, and oil seals are provided between the side-plates 33 and the respective mounting axles 35.

The block 36 is itself pivotally mounted on an elongated spindle 37 carried at the free end of the limbs of a generally "U" shaped pivot arm or support means 38. The wheels 29 are thereby able to pivot about the axis of the spindle 37 so that the two wheels of each inspection device 22 contact the bore of the pipe along lines which are equispaced from each side of a longitudinal plane which passes through the longitudinal axis of the pipe and the longitudinal axis of spindle 37. More specifically, the mounting axles 35 are shown to be of equal length, to be angled with respect to one another, and to lie in the same plane which is normal to the longitudinal axis of the vehicle and which passes through the points of contact between the wheels and the bore of the pipe.

Each ultrasonic probe assembly 30 is resiliently carried by the respective mounting axle 35 and the hollow wheel contains an acoustic coupling means (not shown), such as for example a mixture of glycerol and water. In some instances the glycerol and water mixture may be loaded with particles of carbon, for example, graphite or molybdenum disulphide.

Each ultrasonic probe assembly 30 includes a support structure, consisting of brackets 52 and rods 53, which are arranged to support a nylon block 54 upon which are mounted a plurality of transducers 55, for transmitting ultrasound into the wall of the pipe and for receiving sound scattered or reflected from the wall of the pipe. The block 54 is urged against the inside surface of the rim 32 by a tension spring 56 which is anchored between one of the brackets 52 and a pin 57 secured in a central block 58 which forms part of the spindle 35. The rods 53 are slidably supported in the spindle block 58 for linear movement of the probe assembly. The block 54 is shaped to conform with the shape of the inside surface of the rim 32, so as to ensure that the beams of sound from the transducers 55 enter the pipe wall at a predetermined preferred angle, and that the acoustic coupling medium is permitted to penetrate any gaps between the transducers 55 and the block 54 and between the block 54 and the rim 32. Electrical leads (not shown) from the transducers 55 pass along a bore (not shown) in the spindle 35 through seals which prevent the acoustic coupling medium leaking from the wheel 29 and out through the tapered block 36.

The pivot arm 38 comprises two spaced apart side members 39, 40 connected by a shaft 41. The shaft 41 is connected between plates 28 and is rotatable such that the spindle 37 will move in a radial direction towards and away from the side of tubular vehicle 10. A spring assembly 42 operates on each side member 39, 40 to urge the wheels 29 radially outwardly into engagement with the bore of the pipe. Each spring assembly 42 comprises a compression coil spring 43 mounted on a rod 44 which is rigidly mounted at one end on the carrier plate 28. The coil spring 43 passes through an elongate slot 45 in the pivot arm 38, and urges a thrust pad 46 into engagement with a concave surface of a bracket 47 secured to the pivot arm 38.

Each tapered block 36 is provided with spigots 48 which engage in guideways 49 provided in end stops 50, 51 carried by the carrier plates 28. The guideways 49 are shaped to provide a limit to the pivotal movement of tapered block 36 while allowing some pivotal movement of tapered block 36 when wheels 29 are negotiating irregularities in the pipe surface such as ovality or welds. This guide may also assist in maintaining the wheels 29 correctly aligned relative to the pipe wall so that the wheels 29 contact the pipe wall at points equi-spaced about a longitudinal plane which passes through the longitudinal axis of the vehicle and the longitudinal axis of spindle 37.

Figure 5:
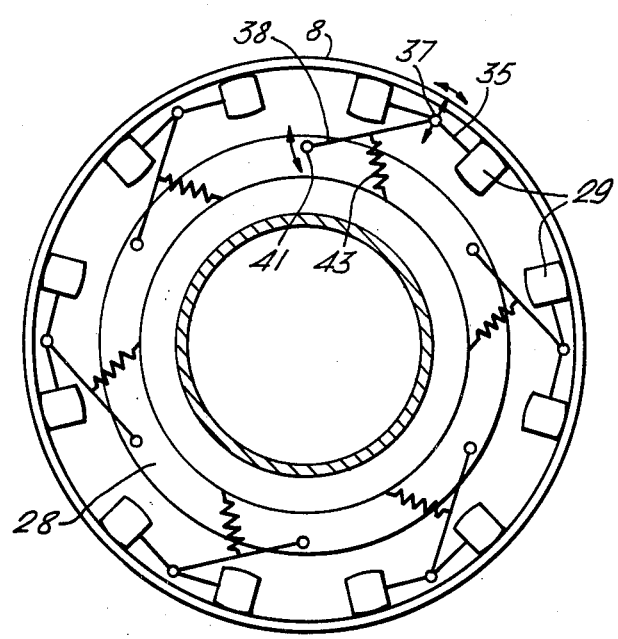
FIG. 5 shows a line diagram of part of the apparatus of FIG. 2.

The movement of the wheels 29 relative to the vehicle may be seen in line diagrammatic form in FIG. 5 to which reference can be made, and in which the wheels 29 are shown in engagement with a pipe 8. As an alternative to the use of pivot support arms, the support arms may be linearly displaceable, for example, in radially-directed grooves.

It is to be understood that the specific design of transducers and their positions inside the wheels may be different from that described above. For example, instead of mounting the ultrasonic probe assembly on rods and employing springs to urge the assembly into contact with rim 32, the block 54 may be dispensed with and the transducers of the ultrasonic probe assembly fixed rigidly to mounting axle 35 and held a small distance away from the rim 32 of the wheel. In this case the wheel is filled with a mixture of glycerol and water loaded with particles of carbon, for example graphite, or molybdenum disulphide. The size of the particles is chosen so as to attenuate slightly the ultrasound, thereby reducing ultrasound reverberation within the wheel after the transmission of an ultrasonic pulse from a transducer.

I claim:

1. A pipe inspection apparatus which is capable of moving along the wall of a pipe, said apparatus including an elongated, generally tubular vehicle,
at least one inspection means mounted on said vehicle, each said inspection means including
a support means, one end of said support means being pivotally mounted to the side of said vehicle and the second end thereof being radially movable towards and away from the side of said vehicle,
an elongated spindle rotatably connected to said second end of said support means, said elongated spindle extending in the longitudinal direction of said vehicle,
an elongated mounting means connected to said elongated spindle, said elongated mounted means being connected to said elongated spindle such that the portions thereof on either side of said elongated spindle are of equal length,
two hollow wheels respectively rotatably mounted on opposite ends of said elongated mounting means so as to be capable of contacting a pipe wall and rolling therealong in a longitudinal direction thereof, and
at least one ultrasonic transducer mounted within each said hollow wheel such that each transducer is aligned in a predetermined position relative to the geometry of the pipe in which said vehicle moves.

2. A pipe inspection apparatus as defined in claim 1, wherein said portions of said elongated mounting means on either side of said elongated spindle are located in a plane which extends normally with respect to the axis of said elongated spindle.

3. A pipe inspection apparatus as defined in claim 2, wherein said portions of said elongated mounting means are angled with respect to one another.

4. A pipe inspection apparatus as defined in claim 3, wherein said portions of said elongated mounting means are angled with respect to one another such that each extends in parallel to a tangent line to the pipe wall where the respective hollow wheel comes in contact therewith.

5. A pipe inspection apparatus as defined in claim 3, including spring means connected between said vehicle side and each said support means to bias said support means, and thus said hollow wheels, away from said vehicle and into contact with a pipe wall.

6. A pipe inspection apparatus as defined in claim 3, wherein said support means comprises a U-shaped arm assembly having two parallel arms and a connecting shaft, wherein said connecting shaft comprises said first end of said support means which is pivotally mounted to the side of said vehicle, and wherein the free ends of said parallel arms comprises the second end of said support means, said elongated spindle being rotatably connected therebetween.

7. A pipe inspection apparatus as defined in claim 6, wherein each hollow wheel includes at least two transducers, one being angled to direct sound in one direction circumferentially through a pipe wall against which the respective wheel is in contact and the second being angled to receive sound from a second direction circumferentially through the pipe wall against which the respective wheel is in contact.

8. A pipe inspection apparatus as defined in claim 3, wherein each hollow wheel includes at least two transducers, and wherein the transducers in each hollow wheel are arranged asymmetrically.

9. A pipe inspection apparatus as defined in claim 3, wherein a tapered block means is located at the connection point between said elongated spindle and said elongated mounting means.

10. A pipe inspection apparatus as defined in claim 1, wherein eight said inspection means are mounted in equispaced fashion circumferentially around the side of said vehicle.

* * * * *